(12) United States Patent
Denyer et al.

(10) Patent No.: US 12,403,266 B1
(45) Date of Patent: Sep. 2, 2025

(54) MEDICAMENT DELIVERY DEVICE

(71) Applicant: Genzyme Corporation, Cambridge, MA (US)

(72) Inventors: Timothy Denyer, Melbourn (GB); James Bradford, Melbourn (GB); Alexander Hee-Hanson, Melbourn (GB); Robert Wilson, Melbourn (GB); Dean Twite, Melbourn (GB); Thomas Lever, Melbourn (GB)

(73) Assignee: Genzyme Corporation, Cambridge, MA (US)

( * ) Notice: Subject to any disclaimer, the term of this patent is extended or adjusted under 35 U.S.C. 154(b) by 0 days.

(21) Appl. No.: 18/819,371

(22) Filed: Aug. 29, 2024

(51) Int. Cl.
*A61M 5/32* (2006.01)
*A61M 5/20* (2006.01)

(52) U.S. Cl.
CPC ............ *A61M 5/322* (2013.01); *A61M 5/20* (2013.01); *A61M 5/3272* (2013.01); *A61M 2005/3267* (2013.01); *A61M 5/3271* (2013.01)

(58) Field of Classification Search
CPC ............... A61M 5/326; A61M 5/3271; A61M 2005/3267; A61M 5/6272
See application file for complete search history.

(56) References Cited

U.S. PATENT DOCUMENTS

| | | | |
|---|---|---|---|
| 4,118,611 A | 10/1978 | Harris | |
| 4,994,045 A * | 2/1991 | Ranford | A61M 5/3271 604/263 |
| 6,547,764 B2 | 4/2003 | Larsen et al. | |
| 8,858,510 B2 * | 10/2014 | Karlsson | A61M 5/3272 604/198 |
| 9,919,107 B2 * | 3/2018 | Imai | A61M 5/326 |
| 12,329,952 B1 | 6/2025 | Denyer et al. | |
| 2002/0133122 A1 | 9/2002 | Giambattista et al. | |
| 2007/0078408 A1 * | 4/2007 | Wang | A61M 5/24 604/110 |

(Continued)

FOREIGN PATENT DOCUMENTS

WO  WO 2022/117682 A1  6/2022

OTHER PUBLICATIONS

Needle-based injection systems for medical use requirements and test methods, Part 1: Needle injection systems, ISO 11608 1:2014(E), Third Edition, Switzerland, ISO, Dec. 15, 2014, pp. 1-13.

(Continued)

*Primary Examiner* — Laura A Bouchelle
(74) *Attorney, Agent, or Firm* — Fish & Richardson P.C.

(57) ABSTRACT

A medicament delivery device has a needle, a body and a needle cover which is axially movable from an initial position to a holding position to a locked position in which the needle cover covers the distal end of the needle. The device has a biasing member configured to bias the needle cover distally, and a guide member configured to rotate relative to the needle cover. One of the guide member and the needle cover has a pin and the other of the guide member and the needle cover has a guide path for guiding the pin. The guide path has a first ramp, a second ramp and a locking abutment surface. When the needle cover is in the locked position then the locking abutment surface is configured to engage the pin to prevent the needle cover from moving proximally away from the locked position.

20 Claims, 6 Drawing Sheets

(56) References Cited

U.S. PATENT DOCUMENTS

2012/0041368 A1    2/2012  Karlsson

OTHER PUBLICATIONS

Speciale et al., "Snap-Through Buckling Mechanism for Frequency-up Conversion in Piezoelectric Energy Harvesting," Applied Sciences, May 23, 2020, 10(10):3614, 18 pages.
U.S. Appl. No. 18/819,222, filed Aug. 29, 2024, Timothy Denyer.
U.S. Appl. No. 18/819,040, filed Aug. 29, 2024, Timothy Denyer.

* cited by examiner

MEDICAMENT DELIVERY DEVICE

TECHNICAL FIELD

This application relates to a medicament delivery device and a method of using a medicament delivery device.

BACKGROUND

Medicament delivery devices are used to deliver a range of medicaments.

In some devices, the device must be held in a holding position at an injection site to ensure that the correct dose of medicament is dispensed from the device, before removing the device from the injection site.

It may be difficult to hold the device in the holding position whilst the medicament is dispensed. This may result in pain, discomfort, a wet injection site, early device removal and/or partial delivery of the medicament.

It is an aspect of the present disclosure to provide an improved medicament delivery device.

SUMMARY

According to a first aspect of the present disclosure, there is provided a medicament delivery device comprising a needle for injecting medicament; a body having a proximal end and a distal end; a needle cover, wherein the needle cover is proximally movable relative to the body from an initial position to a holding position in which the needle protrudes from the distal end of the needle cover for injecting medicament, and wherein the needle cover is distally movable relative to the body from the holding position to a locked position in which the needle cover covers the distal end of the needle; a biasing member configured to bias the needle cover distally; and a guide member configured to rotate relative to the needle cover, wherein one of the guide member and the needle cover comprises a pin and the other of the guide member and the needle cover comprises a guide path for guiding the pin, wherein the guide path comprises a first ramp, a second ramp and a locking abutment surface, wherein the pin is positioned at a first position when the needle cover is in the initial position, and wherein the first ramp is configured to engage the pin when the needle cover moves axially from the initial position towards the holding position for rotating the guide member relative to the needle cover, wherein the pin is positioned at a second position when the needle cover is in the holding position, wherein the second ramp is configured to engage the pin when the needle cover moves axially from the holding position towards the locked position for rotating the guide member relative to the needle cover, wherein the pin is positioned at a third position when the needle cover is in the locked position, wherein the locking abutment surface is configured to engage the pin to prevent the needle cover from moving proximally away from the locked position.

The locking abutment surface may comprise a planar surface which is at an acute angle to the longitudinal axis of the medicament delivery device.

When the pin is in the second position it may engage the first ramp.

The first position may be in the guide path. The guide path may comprise an axially extending portion, wherein the first position is in the axially extending portion. The axially extending portion may be parallel with the longitudinal axis of the medicament delivery device.

The needle cover may be rotationally fixed relative to the body. The guide member may be axially fixed relative to the body.

The first ramp may comprise a planar surface which is at an acute angle to the longitudinal axis of the medicament delivery device. The second ramp may comprise a planar surface which is at an acute angle to the longitudinal axis of the medicament delivery device.

The body may be configured to be gripped by a user.

The needle cover may comprise the pin and the guide member may comprise the guide path. In the initial position the needle cover may cover the distal end of the needle.

The guide member may comprise an outer surface, and wherein the guide path is recessed within the outer surface.

The needle cover may comprise an arm, wherein the pin is provided on the arm. The pin may be provided on the free end of the arm.

The first ramp may be configured to rotate the guide member in a first direction when the needle cover moves axially away from the initial position towards the holding position. The second ramp may be configured to rotate the guide member in the first direction when the needle cover moves axially from the holding position towards the locked position. The locking abutment surface may be configured to prevent rotation of the guide member in a second direction which is counter to the first direction when the pin is in the third position.

The medicament delivery device may be configured to inject greater than 2 ml of medicament. The medicament delivery device may be configured to inject medicament having a viscosity of greater than 25 cP.

The device may comprise a mechanism which automatically causes medicament to be dispensed from the device, wherein when the needle cover moves from the initial position towards the holding position it releases the mechanism and medicament is automatically dispensed from the device.

The device may comprise the medicament.

According to another aspect of the present disclosure, there is provided a method of locking a medicament delivery device after medicament has been dispensed from the medicament delivery device, the method comprising moving a needle cover of the device to a locked position in which the needle cover covers the distal end of a needle of the device, wherein the device comprises a guide member configured to rotate relative to the needle cover, and wherein one of the guide member and the needle cover comprises a pin and the other of the guide member and the needle cover comprises a guide path for guiding the pin, wherein the guide path comprises a locking abutment surface, and wherein when the needle cover is in the locked position then proximal movement of the needle cover away from the locked position is blocked by the pin engaging the locking abutment surface.

The medicament delivery device may have any of the features as described and/or contemplated herein.

According to another aspect of the present disclosure, there is provided a method of using a medicament delivery device, the method comprising removing the medicament delivery device from an injection site, wherein removing the medicament delivery device from the injection site causes a needle cover of the device to move to a locked position in which the needle cover covers the distal end of a needle of the device, wherein the device comprises a guide member configured to rotate relative to the needle cover, and wherein one of the guide member and the needle cover comprises a pin and the other of the guide member and the needle cover comprises a guide path comprising a locking abutment surface, and wherein when the needle cover is in the locked position then proximal movement of the needle cover away from the locked position is blocked by the pin engaging the locking abutment surface.

The method may further comprise the preceding step of pressing the medicament delivery device against the injection site to move the needle cover from an initial position to a holding position for dispensing medicament from the device.

The method may further comprise holding the medicament delivery device in the holding position whilst medicament is dispensed from the device.

The guide path may further comprise a first ramp which engages the pin when the needle cover moves axially from the initial position towards the holding position for rotating the guide member relative to the needle cover.

The guide path may further comprise a second ramp which engages the pin when the needle cover moves from the holding position towards the locked position for rotating the guide member relative to the needle cover.

The movement of the needle cover from the initial position to the holding position may cause medicament to be dispensed from the device via the needle.

The device may comprise a mechanism configured to dispense medicament from the device via the needle when the needle cover reaches a predetermined axial position. Movement of the needle cover from the initial position to the holding position may trigger the mechanism to dispense medicament from the device via the needle.

The medicament delivery device may comprise a container for containing the medicament. The medicament may be located in the container. The container may be a syringe. The syringe may comprise the needle. The container may be a cartridge which is initially separated from the needle when the needle cover is in the initial position.

BRIEF DESCRIPTION OF THE FIGURES

Embodiments will now be described, by way of example only, with reference to the accompanying drawings, in which.

DETAILED DESCRIPTION

Figure 1A:
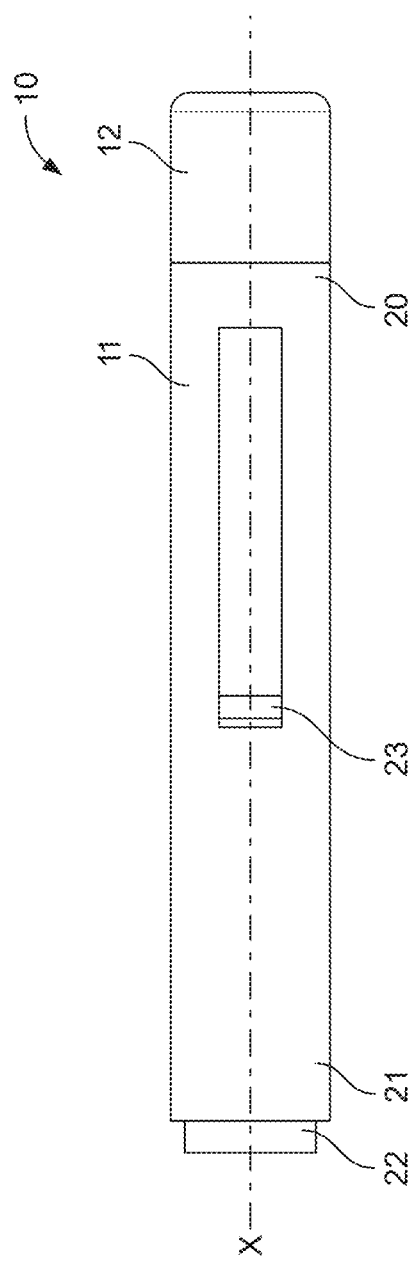
FIG. 1A shows an injector device with a cap attached.

A drug delivery device, as described herein, may be configured to inject a medicament into a patient. For example, delivery could be sub-cutaneous, intra-muscular, or intravenous. Such a device could be operated by a patient or care-giver, such as a nurse or physician, and can include various types of safety syringe, pen-injector, or auto-injector. The device can include a cartridge-based system that requires piercing a sealed ampule before use. Volumes of medicament delivered with these various devices can range from about 0.5 ml to about 2 ml. Yet another device can include a large volume device ("LVD") or patch pump, configured to adhere to a patient's skin for a period of time (e.g., about 5, 15, 30, 60, or 120 minutes) to deliver a "large" volume of medicament (typically about 2 ml to about 10 ml).

In combination with a specific medicament, the presently described devices may also be customized in order to operate within required specifications. For example, the device may be customized to inject a medicament within a certain time period (e.g., about 3 to about 20 seconds for auto-injectors, and about 10 minutes to about 60 minutes for an LVD). Other specifications can include a low or minimal level of discomfort, or to certain conditions related to human factors, shelf-life, expiry, biocompatibility, environmental considerations, etc. Such variations can arise due to various factors, such as, for example, a drug ranging in viscosity from about 3 cP to about 50 cP. Consequently, a drug delivery device will often include a hollow needle ranging from about 25 to about 31 Gauge in size. Common sizes are 27 and 29 Gauge.

The delivery devices described herein can also include one or more automated functions. For example, one or more of needle insertion, medicament injection, and needle retraction can be automated. Energy for one or more automation steps can be provided by one or more energy sources. Energy sources can include, for example, mechanical, pneumatic, chemical, or electrical energy. For example, mechanical energy sources can include springs, levers, elastomers, or other mechanical mechanisms to store or release energy. One or more energy sources can be combined into a single device. Devices can further include gears, valves, or other mechanisms to convert energy into movement of one or more components of a device.

The one or more automated functions of an auto-injector may each be activated via an activation mechanism. Such an activation mechanism can include one or more of a button, a lever, a needle sleeve, or other activation component. Activation of an automated function may be a one-step or multi-step process. That is, a user may need to activate one or more activation components in order to cause the automated function. For example, in a one-step process, a user may depress a needle sleeve against their body in order to cause injection of a medicament. Other devices may require a multi-step activation of an automated function. For example, a user may be required to depress a button and retract a needle shield in order to cause injection.

In addition, activation of one automated function may activate one or more subsequent automated functions, thereby forming an activation sequence. For example, activation of a first automated function may activate at least two of needle insertion, medicament injection, and needle retraction. Some devices may also require a specific sequence of steps to cause the one or more automated functions to occur. Other devices may operate with a sequence of independent steps.

Some delivery devices can include one or more functions of a safety syringe, pen-injector, or auto-injector. For example, a delivery device could include a mechanical energy source configured to automatically inject a medicament (as typically found in an auto-injector) and a dose setting mechanism (as typically found in a pen-injector).

Figure 1B:
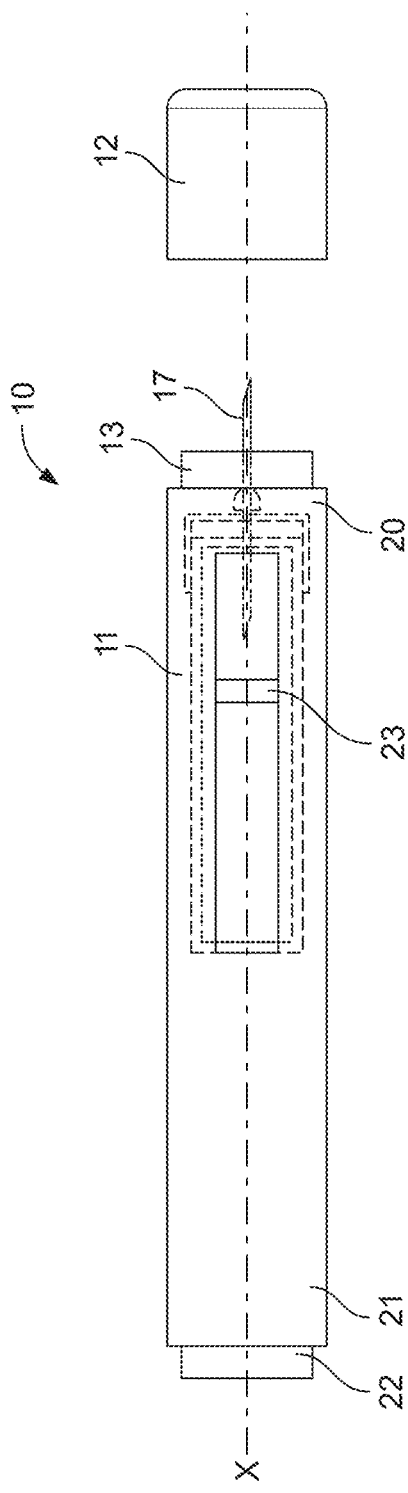
FIG. 1B shows the injector device of FIG. 1A with the cap removed.

According to some embodiments of the present disclosure, an exemplary drug delivery device 10 is shown in FIGS. 1A & 1B. Device 10, as described above, is configured to inject a medicament into a patient's body. Device 10 includes a housing 11 which typically contains a reservoir containing the medicament to be injected (e.g., a syringe) and the components required to facilitate one or more steps of the delivery process. Device 10 can also include a cap assembly 12 that can be detachably mounted to the housing 11. Typically a user must remove cap 12 from housing 11 before device 10 can be operated.

As shown, housing 11 is substantially cylindrical and has a substantially constant diameter along the longitudinal axis X. The housing 11 has a distal region 20 and a proximal region 21. The term "distal" refers to a location that is relatively closer to a site of injection, and the term "proximal" refers to a location that is relatively further away from the injection site.

Device 10 can also include a needle sleeve 13 coupled to housing 11 to permit movement of sleeve 13 relative to housing 11. For example, sleeve 13 can move in a longitudinal direction parallel to longitudinal axis X. Specifically, movement of sleeve 13 in a proximal direction can permit a needle 17 to extend from distal region 20 of housing 11.

Insertion of needle 17 can occur via several mechanisms. For example, needle 17 may be fixedly located relative to housing 11 and initially be located within an extended needle sleeve 13. Proximal movement of sleeve 13 by placing a distal end of sleeve 13 against a patient's body and moving housing 11 in a distal direction will uncover the distal end of needle 17. Such relative movement allows the distal end of needle 17 to extend into the patient's body. Such insertion is termed "manual" insertion as needle 17 is manually inserted via the patient's manual movement of housing 11 relative to sleeve 13.

Another form of insertion is "automated," whereby needle 17 moves relative to housing 11. Such insertion can be triggered by movement of sleeve 13 or by another form of activation, such as, for example, a button 22. As shown in FIGS. 1A & 1B, button 22 is located at a proximal end of housing 11. However, in other embodiments, button 22 could be located on a side of housing 11.

Other manual or automated features can include drug injection or needle retraction, or both. Injection is the process by which a bung or piston 23 is moved from a proximal location within a syringe (not shown) to a more distal location within the syringe in order to force a medicament from the syringe through needle 17. In some embodiments, a drive spring (not shown) is under compression before device 10 is activated. A proximal end of the drive spring can be fixed within proximal region 21 of housing 11, and a distal end of the drive spring can be configured to apply a compressive force to a proximal surface of piston 23. Following activation, at least part of the energy stored in the drive spring can be applied to the proximal surface of piston 23. This compressive force can act on piston 23 to move it in a distal direction. Such distal movement acts to compress the liquid medicament within the syringe, forcing it out of needle 17.

Following injection, needle 17 can be retracted within sleeve 13 or housing 11. Retraction can occur when sleeve 13 moves distally as a user removes device 10 from a patient's body. This can occur as needle 17 remains fixedly located relative to housing 11. Once a distal end of sleeve 13 has moved past a distal end of needle 17, and needle 17 is covered, sleeve 13 can be locked. Such locking can include locking any proximal movement of sleeve 13 relative to housing 11. Another form of needle retraction can occur if needle 17 is moved relative to housing 11. Such movement can occur if the syringe within housing 11 is moved in a proximal direction relative to housing 11. This proximal movement can be achieved by using a retraction spring (not shown), located in distal region 20. A compressed retraction spring, when activated, can supply sufficient force to the syringe to move it in a proximal direction. Following sufficient retraction, any relative movement between needle 17 and housing 11 can be locked with a locking mechanism. In addition, button 22 or other components of device 10 can be locked as required.

Figure 2:
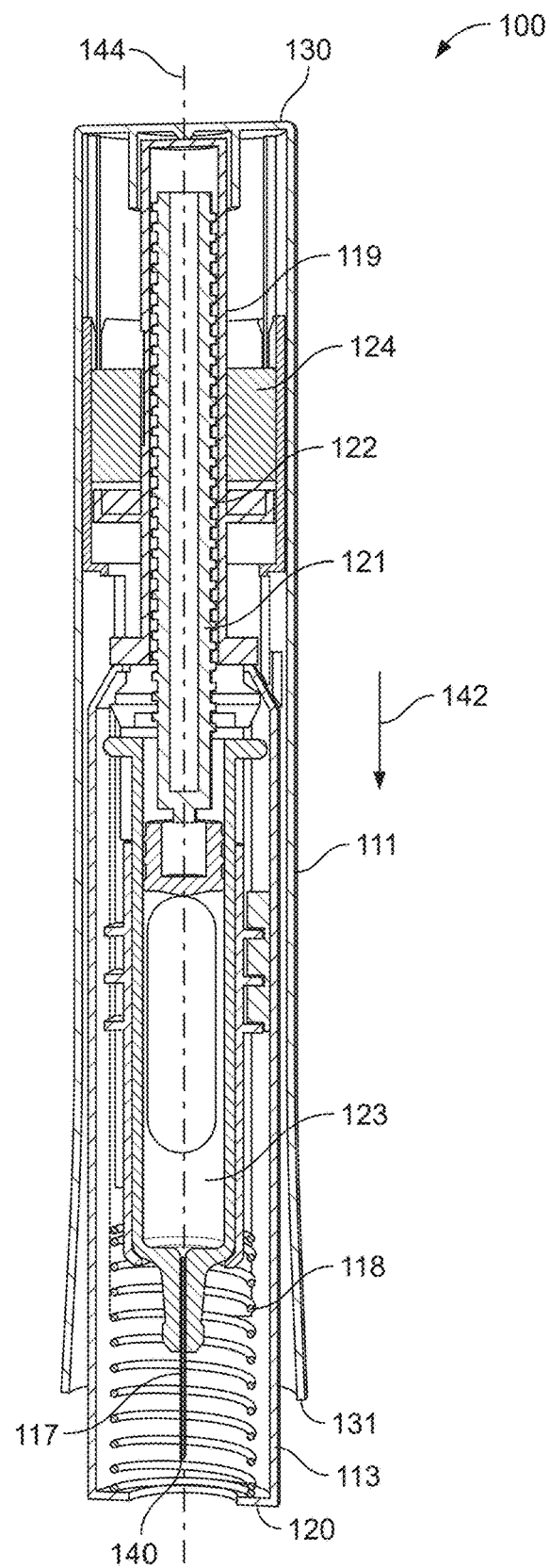
FIG. 2 shows a medicament delivery device.

FIG. 2 shows a simplified view of a medicament delivery device 100. The medicament delivery device 100 has a needle 117 for injecting medicament, a body 111 having a proximal end 130 and a distal end 131, and a needle cover 113. The needle 117 has a distal end 140. The needle cover 113 is proximally movable relative to the body 111 between an initial position, in which the needle cover 113 covers the distal end 140 of the needle, and a holding position for dispensing medicament from the device. The device 100 extends along an axis 144.

The device 100 is shown in the initial position in FIG. 2. In the holding position the needle cover 113 is located proximally relative to the initial position. In the holding position the needle 117 protrudes from the distal end 120 of the needle cover 113.

The medicament delivery device further comprises a biasing member such as a spring 118 configured to bias the needle cover 113 axially in the distal direction. The distal direction is indicated by the direction of the arrow 142 in FIG. 2.

The medicament delivery device has a plunger 121 which is axially movable within a syringe 123 of the device to dispense medicament from the syringe 123 via the needle 117.

The medicament delivery device has a collar 119. The collar 119 is axially fixed relative to the body 111. The collar 119 interfaces with the plunger 121 via a screw thread 122. The medicament delivery device 100 has a biasing member such as a spring 124, that is configured to rotate the collar 119 when the spring 124 is released. The spring 124 may be a torsion spring. The spring 124 is released when the needle cover 113 reaches a predetermined axial displacement with a release mechanism (not shown). The rotation of the collar 119 causes the plunger 121 to move distally within the syringe 123, in view of the screw thread 122, to thereby dispense medicament from the syringe 123 via the needle 117.

The needle cover 113 is pressed against an injection site, thereby moving the needle cover 113 axially into the body 111 and uncovering the needle 117. The axial displacement of the needle cover 113 causes the release of the spring 124 which rotates the collar 119. The rotation of the collar 119 moves the plunger 121 axially within the syringe 123 to dispense the medicament via the needle 117.

The device 100 is pressed against the injection site 125, to hold the needle cover 113 at the holding position whilst the medicament is dispensed from the device.

After the medicament has been dispensed, the device 100 is removed from the injection site. The needle cover 113 moves distally under the force of the spring 118 to a locked position. In the locked position, the needle cover 113 covers the distal end 140 of the needle. In the locked position, the needle cover is prevented from moving proximally.

The medicament delivery device 100 is configured to inject greater than 2 ml of medicament and/or the medicament delivery device 100 is configured to inject medicament having a viscosity of greater than 25 cP.

Figure 3A:
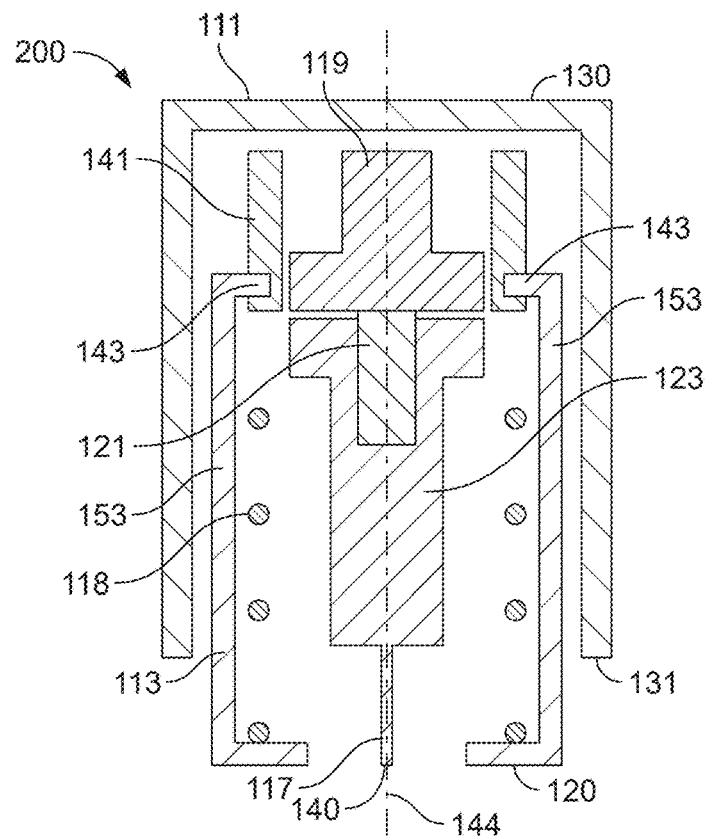
FIG. 3A shows a simplified view of an example medicament delivery device when the needle cover is in the initial position.

FIG. 3A shows a simplified view of a medicament delivery device 200. The features described and/or contemplated in relation to the medicament delivery device 200 may be incorporated in the medicament delivery device 100 as described and/or contemplated above.

The features described and/or contemplated in relation to the medicament delivery device 200 may be incorporated in another medicament delivery device, for example a medicament delivery device having a different mechanism for dispensing medicament to that described in relation to the medicament delivery device 100, and/or a medicament delivery device which is configured to inject 2 ml or less of medicament and/or a medicament delivery device which is configured to inject medicament having a viscosity of 25 cP or less, and/or a medicament delivery device in which the medicament is contained in a cartridge which is initially separated from the needle when the needle cover is in the initial position.

In FIGS. 3A to 3B, 4A to 4B, 5A to 5B and FIG. 6, the reference numerals correspond to corresponding features described and/or contemplated above in relation to FIG. 2.

In FIG. 3A the medicament delivery device 200 is shown in an initial position. The medicament delivery device 200 has a needle 117 for injecting medicament, a body 111 having a proximal end 130 and a distal end 131, and a needle cover 113. The body 111 is configured to be gripped by a user.

The needle cover 113 is proximally movable relative to the body 111 from an initial position to a holding position. In the initial position, as shown for example in FIG. 3A, the needle cover 113 covers the distal end of the needle. In the holding position, as shown for example in FIG. 4A, the needle 117 protrudes from the distal end of the needle cover for injecting medicament. When the needle cover moves from the initial position to the holding position it releases a mechanism, such as the mechanism described and/or contemplated in relation to FIG. 2, which automatically causes medicament to be dispensed from the device 200. The needle cover 113 is held in the holding position, for example for a predetermined period of time, whilst the medicament is dispensed from the device.

Figure 5A:
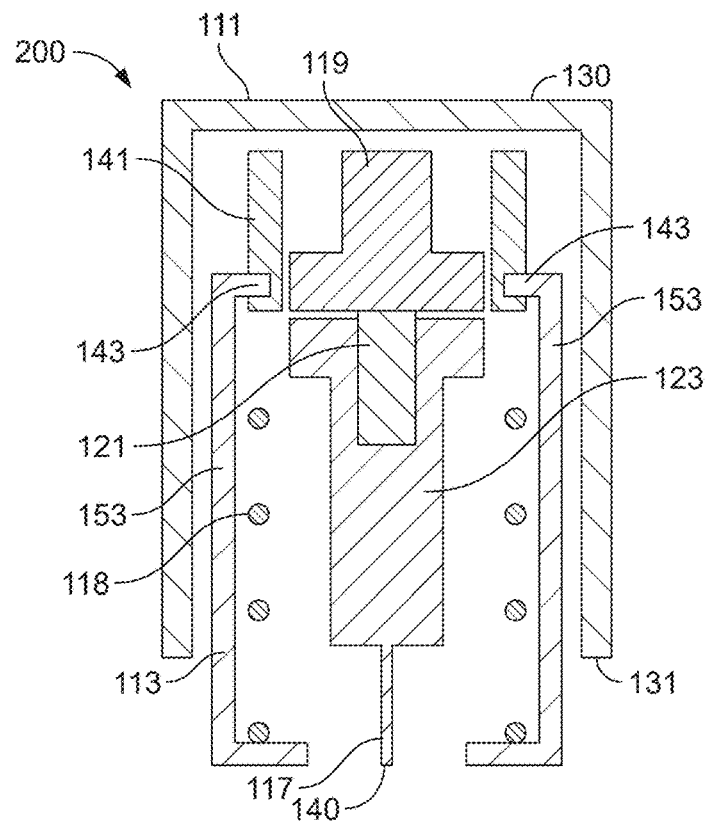
FIG. 5A shows a simplified view of the medicament delivery device of FIG. 3A when the needle cover is in the locked position.

The needle cover 113 is distally movable relative to the body 111 from the holding position to a locked position, as shown for example in FIG. 5A, in which the needle cover 113 covers the distal end 140 of the needle 117.

The medicament delivery device 200 has a biasing member such as a spring 118 configured to bias the needle cover 113 distally.

The medicament delivery device 200 has a guide member 141 configured to rotate relative to the needle cover 113. The guide member 141 has a guide path 154. The guide path 154 has a first ramp 148, a second ramp 149 and a locking abutment surface 150.

The needle cover 113 is rotationally fixed relative to the body 111. In another embodiment, the needle cover 113 is rotatable relative to the body 111. The guide member 141 is axially fixed relative to the body 111. In another embodiment, the guide member 141 is axially movable relative to the body 111.

The needle cover 113 has a pin 143 configured to engage and move within the guide path 154. The needle cover has an arm 153. The arm 153 extends proximally from a sleeve 154 of the needle cover. The pin 143 is provided on the free end of the arm. In another embodiment, the pin 143 is located distally from the free end of the arm 153.

The medicament delivery device has two arms 153 each of which has a pin 143 located in a separate guide path 154. In another embodiment just one arm 153 and one guide path 154 may be provided or more than two arms and corresponding guide paths may be provided. The features of just one arm 153 and guide path 154 will be described herein but if other arms and guide paths are present then they may have the same features as described herein in relation to the one arm 153 and guide path 154.

In another embodiment, the needle cover 113 has a different construction. For example, the arms may 153 may not be present. The needle cover 113 may be in the form of a circular sleeve. The pin 143 may be provided on an outer surface of the circular sleeve, for example.

Figure 3B:
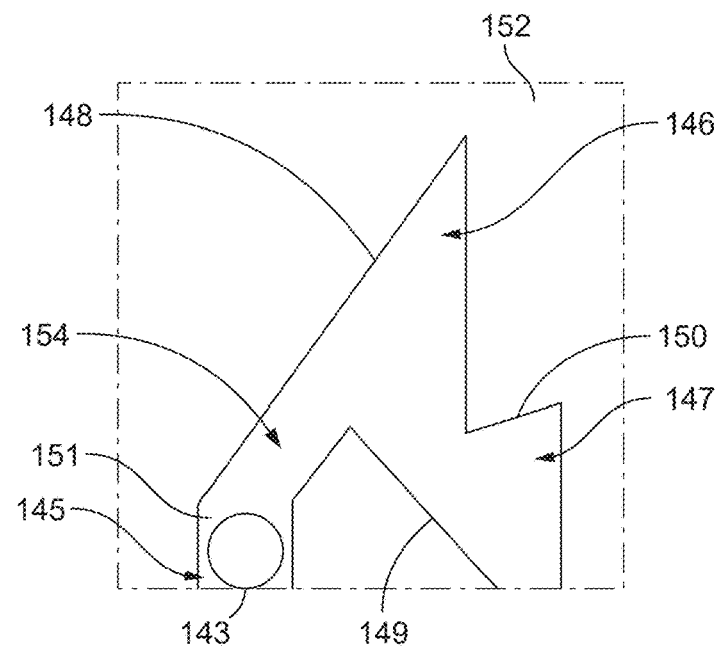
FIG. 3B shows a view of the guide path of the medicament delivery device of FIG. 3A, indicating the position of the pin when the needle cover is in the initial position.

The pin 143 is positioned at a first position 145 when the needle cover 113 is in the initial position. The first position 145 is indicated in FIG. 3B. The first position 145 is in the guide path 154. The guide path 154 has an axially extending portion 151. The first position 145 is in the axially extending portion 151. The axially-extending portion 151 is parallel to the longitudinal axis 144 of the medicament delivery device. In another embodiment, the axially-extending portion 151 is at an acute angle to the longitudinal axis 144 of the medicament delivery device. In another embodiment, the axially-extending portion 151 is not present and the pin 143 engages the first ramp 148 when the needle cover 113 is in the initial position, for example.

In another embodiment, the first position 145 of the pin 143, when the needle cover is in the initial position, is external to the guide path 154, for example the pin 143 could drop into guide path 154 after an initial axial movement.

The guide path 154 has a first ramp 148 configured to engage the pin 143 when the needle cover 113 moves axially from the initial position towards the holding position for rotating the guide member 141 relative to the needle cover 113. The first ramp 148 is located proximally of the first position 145. The first ramp 148 extends proximally away from the first position 145. The first ramp 148 rotates the guide member 141 relative to the needle cover 133 when the pin 143 engages and travels along the first ramp 148 and the needle cover 133 moves from the initial position towards the holding position. In another embodiment the first ramp 148 may extend distally from the first position as well as proximally from the first position.

Figure 4A:
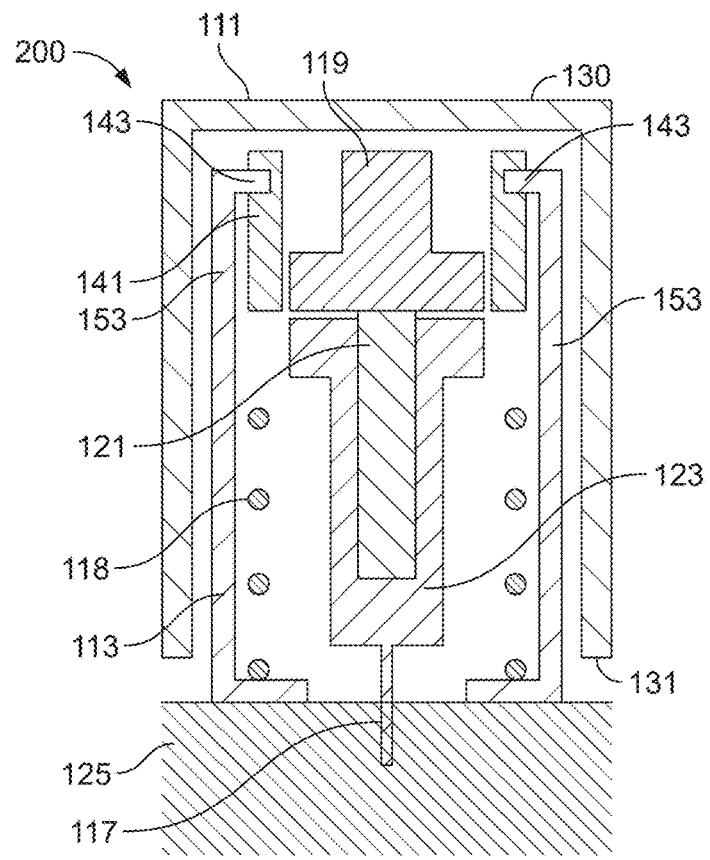
FIG. 4A shows a simplified view of the medicament delivery device of FIG. 3A when the needle cover is in the holding position.
Figure 4B:
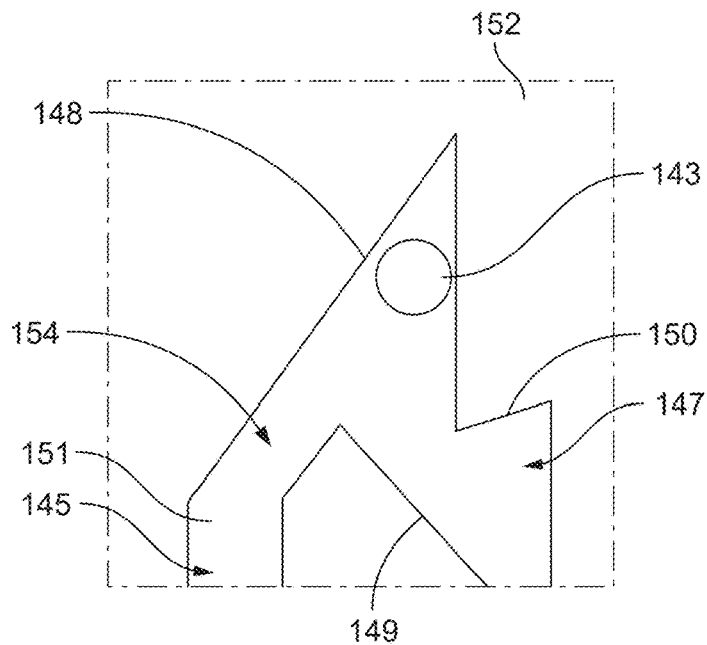
FIG. 4B shows a view of the guide path of the medicament delivery device of FIG. 3A, indicating the position of the pin when the needle cover is in the holding position.

The pin 143 is positioned at a second position 146 in the guide path 154 when the needle cover 133 is in the holding position. The second position is indicated in FIG. 4B. When the pin 143 is in the second position 146 it engages the first ramp 148. In another embodiment, the first ramp 148 may connect to an axially-extending portion which is parallel with the longitudinal axis of the device, for example, and the second position 146 may be in the axially-extending portion.

The guide path 150 has a second ramp 149 configured to engage the pin 143 when the needle cover 133 moves axially from the holding position towards the locked position for rotating the guide member 141 relative to the needle cover 113. The second ramp 149 is located distally of the second position. The second ramp 149 extends distally away from the second position. The second ramp 149 rotates the guide member 141 relative to the needle cover 133 when the pin 143 engages and travels along the second ramp 149 and the needle cover 133 moves from the holding position towards the locked position.

The first ramp 148 is a planar surface which is at an acute angle to the longitudinal axis 144 of the medicament delivery device. The second ramp 149 is a planar surface which is at an acute angle to the longitudinal axis 144 of the medicament delivery device. In another embodiment the first ramp 148 and/or the second ramp 149 comprises a curved surface.

Figure 5B:
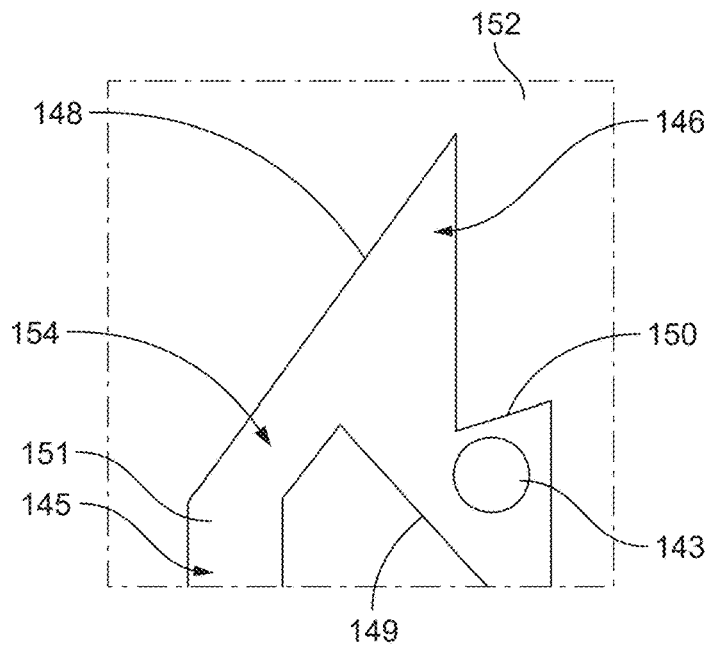
FIG. 5B shows a view of the guide path of the medicament delivery device of FIG. 3A, indicating the position of the pin when the needle cover is in the locked position.

The pin 143 is positioned at a third position 147 in the guide path 154 when the needle cover 113 is in the locked position. The third position 147 is indicated in FIG. 5B. The guide path 154 has a locking abutment surface 150 located proximally of the third position 147. The locking abutment surface 150 is configured to engage the pin 143 to prevent the needle cover 113 from moving proximally away from the locked position.

The locking abutment surface 150 extends distally from the third position at an acute angle to the longitudinal axis 144 of the medicament delivery device 200. In another embodiment, the locking abutment surface 150 may be perpendicular to the longitudinal axis 144 of the medicament delivery device.

If the medicament delivery device 200 did not have a locking functionality for preventing proximal movement of the needle cover 113 after use, then the spring 118 would need to be much stronger to ensure that the distal end 140 of the needle remains covered once the device has been used. Therefore, having the locking functionality in the device means that the spring 118 can be weaker, which consequently reduces the force that is required to be exerted to hold the device in the holding position.

The guide member 141 has an outer surface 152. The guide path 154 is recessed within the outer surface 152. In another embodiment, the guide path 154 may be raised, such as located radially-outwardly, from the outer surface 152.

The first ramp 148 is configured to rotate the guide member 141 in a first direction when the needle cover 113 moves from the initial position towards the holding position. The second ramp 149 is configured to rotate the guide member 141 in the first direction when the needle cover 113 moves from the holding position towards the locked position. The locking abutment surface 150 is configured to prevent rotation of the guide member 141 in a second direction which is counter to the first direction when the pin 143 is in the third position. In another embodiment, for example if the locking abutment surface 150 is perpendicular to the longitudinal axis 144 then the locking abutment surface does not prevent rotation of the guide member 141 in the second direction.

In another embodiment, the first ramp 148 is configured to rotate the guide member 141 in a first direction when the needle cover 113 moves from the initial position towards the holding position and the second ramp 149 is configured to rotate the guide member in a second direction which is counter to the first direction when the needle cover 113 moves from the holding position towards the locked position.

The guide path 154 provides different paths for the needle cover before and after the medicament has been dispensed from the device.

In the embodiments described and/or contemplated above the needle cover 113 comprises the pin 143 and the guide member 141 comprises the guide path 154. However, in other embodiments, the guide member 141 comprises the pin 143 and the needle cover 113 comprises the guide path 154. These other embodiments may have corresponding features to those described and/or contemplated herein in which the needle cover comprises the pin and the guide member comprises the guide path.

The medicament delivery device may have a cap (not shown) which covers the distal end of the needle cover 113 and which must be removed before use.

In use, the needle cover 113 is pressed against an injection site 125, for example by a user holding the body 111, to move the needle cover 113 from the initial position to the holding position. The pin 143 is in a first position when the needle cover 113 is in the initial position. When the needle cover moves from the initial position to the holding position then the pin 143 moves in the guide path 154 from the axially-extending portion 151 (if present) to the first ramp 148. The pin 143 engages the first ramp 148 and rotates the guide member 141 relative to the needle cover 113 and the body 111 when the pin 143 engages the first ramp 148 and travels along the first ramp 148 as the needle cover 113 is moved axially towards the holding position.

When the needle cover 113 is in the holding position then the medicament delivery device 200 is held against the injection site 125 whilst the medicament is dispensed from the device 200. The pin 143 is in the second position 146 when the needle cover 113 is in the holding position.

After the medicament has been dispensed, the medicament delivery device 200 is removed from the injection site 125. The needle cover moves distally from the holding position towards the locked position under the force of the biasing member 118.

When the needle cover moves from the holding position to the locked position then the pin 143 engages the second ramp 149 and rotates the guide member 141 relative to the needle cover 113.

When the needle cover 113 is in the locked position then the locking abutment surface 150 prevents the needle cover 113 from moving proximally away from the locked position.

Figure 6:
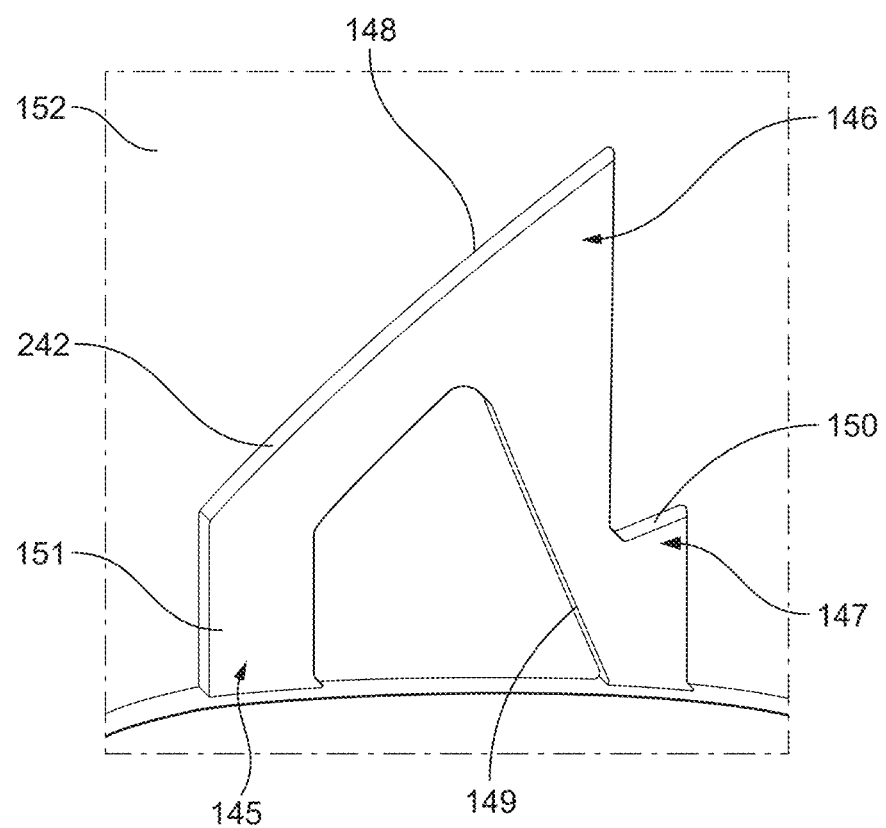
FIG. 6 shows a perspective view of a guide path for a medicament delivery device.

FIG. 6 shows a perspective view of a guide path 242 for a medicament delivery device. The guide path 242 has corresponding features to those described in relation to the guide path 154 but it has a slightly different shape. The reference numerals in FIG. 6 correspond to corresponding features described and/or contemplated above in relation to FIGS. 3A, 3B, 4A, 4B, 5A and 5B.

An example method of using the medicament delivery device 200 will now be described.

The method may include removing the cap (if present) from the medicament delivery device. The method includes pressing the medicament delivery device against the injection site to move the needle cover 113 from an initial position to a holding position for dispensing medicament from the device.

The method then includes holding the medicament delivery device 200 in the holding position whilst medicament is dispensed from the device.

The method then includes removing the medicament delivery device 200 from the injection site. Removing the medicament delivery device from the injection site causes the needle cover 113 of the device to move to a locked position. The needle cover 113 is moved to the locked position under the force of the biasing member 118. In the locked position proximal movement of the needle cover 113 away from the locked position is blocked by the pin engaging the locking abutment surface 150.

LIST OF FEATURES

10—Device
11—housing
12—cap
13—needle sleeve
17—needle
20—distal region
21—proximal region
22—button
23—piston
100—Device
111—body
113—needle cover
117—needle
118—spring
119—collar
120—distal end of needle cover
121—plunger
122—screw thread
123—syringe
124—spring
125—injection site
130—proximal end of body
131—distal end of body
140—distal end of needle
141—guide member 143—pin
144—axis
145—first position
146—second position
147—third position
148—first ramp
149—second ramp
150—locking abutment surface
151—axially-extending portion
152—outer surface
153—arm
154—guide path
200—device
242—guide path The terms "drug" or "medicament" are used synonymously herein and describe a pharmaceutical formulation containing one or more active pharmaceutical ingredients or pharmaceutically acceptable salts or solvates thereof, and optionally a pharmaceutically acceptable carrier. An active pharmaceutical ingredient ("API"), in the broadest terms, is a chemical structure that has a biological effect on humans or animals. In pharmacology, a drug or medicament is used in the treatment, cure, prevention, or diagnosis of disease or used to otherwise enhance physical or mental well-being. A drug or medicament may be used for a limited duration, or on a regular basis for chronic disorders.

As described below, a drug or medicament can include at least one API, or combinations thereof, in various types of formulations, for the treatment of one or more diseases. Examples of API may include small molecules having a molecular weight of 500 Da or less; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more drugs are also contemplated.

The drug or medicament may be contained in a primary package or "drug container" adapted for use with a drug delivery device. The drug container may be, e.g., a cartridge, syringe, reservoir, or other solid or flexible vessel configured to provide a suitable chamber for storage (e.g., short- or long-term storage) of one or more drugs. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about −4° C. to about 4° C.). In some instances, the drug container may be or may include a dual-chamber cartridge configured to store two or more components of the pharmaceutical formulation to-be-administered (e.g., an API and a diluent, or two different drugs) separately, one in each chamber. In such instances, the two chambers of the dual-chamber cartridge may be configured to allow mixing between the two or more components prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively or in addition, the two chambers may be configured to allow mixing as the components are being dispensed into the human or animal body.

The drugs or medicaments contained in the drug delivery devices as described herein can be used for the treatment and/or prophylaxis of many different types of medical disorders. Examples of disorders include, e.g., diabetes mellitus or complications associated with diabetes mellitus such as diabetic retinopathy, thromboembolism disorders such as deep vein or pulmonary thromboembolism. Further examples of disorders are acute coronary syndrome (ACS), angina, myocardial infarction, cancer, macular degeneration, inflammation, hay fever, atherosclerosis and/or rheumatoid arthritis. Examples of APIs and drugs are those as described in handbooks such as Rote Liste 2014, for example, without limitation, main groups 12 (anti-diabetic drugs) or 86 (oncology drugs), and Merck Index, 15th edition.

Examples of APIs for the treatment and/or prophylaxis of type 1 or type 2 diabetes mellitus or complications associated with type 1 or type 2 diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the terms "analogue" and "derivative" refers to a polypeptide which has a molecular structure which formally can be derived from the structure of a naturally occurring peptide, for example that of human insulin, by deleting and/or exchanging at least one amino acid residue occurring in the naturally occurring peptide and/or by adding at least one amino acid residue. The added and/or exchanged amino acid residue can either be codable amino acid residues or other naturally occurring residues or purely synthetic amino acid residues. Insulin analogues are also referred to as "insulin receptor ligands". In particular, the term "derivative" refers to a polypeptide which has a molecular structure which formally can be derived from the structure of a naturally occurring peptide, for example that of human insulin, in which one or more organic substituent (e.g., a fatty acid) is bound to one or more of the amino acids. Optionally, one or more amino acids occurring in the naturally occurring peptide may have been deleted and/or replaced by other amino acids, including non-codeable amino acids, or amino acids, including non-codeable, have been added to the naturally occurring peptide. Examples of insulin analogues are Gly (A21), Arg (B31), Arg (B32) human insulin (insulin glargine); Lys (B3), Glu (B29) human insulin (insulin glulisine); Lys (B28), Pro (B29) human insulin (insulin lispro); Asp (B28) human insulin (insulin aspart); human insulin, wherein proline in position B28 is replaced by Asp, Lys, Leu, Val or Ala and wherein in position B29 Lys may be replaced by Pro; Ala (B26) human insulin; Des (B28-B30) human insulin; Des (B27) human insulin and Des (B30) human insulin.

Examples of insulin derivatives are, for example, B29-N-myristoyl-des (B30) human insulin, Lys (B29) (N-tetradecanoyl)-des (B30) human insulin (insulin detemir, Levemir®); B29-N-palmitoyl-des (B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-gamma-glutamyl)-des (B30) human insulin, B29-N-omega-carboxypentadecanoyl-gamma-L-glutamyl-des (B30) human insulin (insulin degludec, Tresiba®); B29-N-(N-lithocholyl-gamma-glutamyl)-des (B30) human insulin; B29-N-(ω-carboxyheptadecanoyl)-des (B30) human insulin and B29-N-(ω-carboxyheptadecanoyl) human insulin.

Examples of GLP-1, GLP-1 analogues and GLP-1 receptor agonists are, for example, Lixisenatide (Lyxumia®), Exenatide (Exendin-4, Byetta®, Bydureon®, a 39 amino acid peptide which is produced by the salivary glands of the Gila monster), Liraglutide (Victoza®), Semaglutide, Taspoglutide, Albiglutide (Syncria®), Dulaglutide (Trulicity®), rExendin-4, CJC-1134-PC, PB-1023, TTP-054, Langlenatide/HM-11260C (Efpeglenatide), HM-15211, CM-3, GLP-1 Eligen, ORMD-0901, NN-9423, NN-9709, NN-9924, NN-9926, NN-9927, Nodexen, Viador-GLP-1, CVX-096, ZYOG-1, ZYD-1, GSK-2374697, DA-3091 March-701, MAR709, ZP-2929, ZP-3022, ZP-DI-70, TT-401 (Pegapamodtide), BHM-034. MOD-6030, CAM-2036, DA-15864, ARI-2651, ARI-2255, Tirzepatide (LY3298176), Bamadutide (SAR425899), Exenatide-XTEN and Glucagon-Xten. An example of an oligonucleotide is, for example: mipomersen sodium (Kynamro®), a caperturesterol-reducing antisense therapeutic for the treatment of familial hypercapturesterolemia or RG012 for the treatment of Alport syndrom. Examples of DPP4 inhibitors are Linagliptin, Vildagliptin, Sitagliptin, Denagliptin, Saxagliptin, Berberine.

Examples of hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Examples of polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20 (Synvisc®), a sodium hyaluronate.

The term "antibody", as used herein, refers to an immunoglobulin molecule or an antigen-binding portion thereof. Examples of antigen-binding portions of immunoglobulin molecules include F (ab) and F(ab')2 fragments, which retain the ability to bind antigen. The antibody can be polyclonal, monoclonal, recombinant, chimeric, de-immunized or humanized, fully human, non-human, (e.g., murine), or single chain antibody. In some embodiments, the antibody has effector function and can fix complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region. The term antibody also includes an antigen-binding molecule based on tetravalent bispecific tandem immunoglobulins (TBTI) and/or a dual variable region antibody-like binding protein having cross-over binding region orientation (CODV).

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that are useful in the present invention include, for example, Fab fragments, F(ab')2 fragments, scFv (single-chain Fv) fragments, linear antibodies, monospecific or multispecific antibody fragments such as bispecific, trispecific, tetraspecific and multispecific antibodies (e.g., diabodies, triabodies, tetrabodies), monovalent or multivalent antibody fragments such as bivalent, trivalent, tetravalent and multivalent antibodies, minibodies, chelating recombinant antibodies, tribodies or bibodies, intrabodies, nanobodies, small modular immunopharmaceuticals (SMIP), binding-domain immunoglobulin fusion proteins, camelized antibodies, and VHH containing antibodies. Additional examples of antigen-binding antibody fragments are known in the art. The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen.

Examples of antibodies are anti PCSK-9 mAb (e.g., Alirocumab), anti IL-6 mAb (e.g., Sarilumab), and anti IL-4 mAb (e.g., Dupilumab).

Pharmaceutically acceptable salts of any API described herein are also contemplated for use in a drug or medicament in a drug delivery device. Pharmaceutically acceptable salts are for example acid addition salts and basic salts.

Those of skill in the art will understand that modifications (additions and/or removals) of various components of the APIs, formulations, apparatuses, methods, systems and embodiments described herein may be made without departing from the full scope and spirit of the present invention, which encompass such modifications and any and all equivalents thereof.

An example drug delivery device may involve a needle-based injection system as described in Table 1 of section 5.2 of ISO 11608-1: 2014 (E). As described in ISO 11608-1: 2014 (E), needle-based injection systems may be broadly distinguished into multi-dose container systems and single-dose (with partial or full evacuation) container systems. The container may be a replaceable container or an integrated non-replaceable container.

As further described in ISO 11608-1: 2014 (E), a multi-dose container system may involve a needle-based injection device with a replaceable container. In such a system, each container holds multiple doses, the size of which may be fixed or variable (pre-set by the user). Another multi-dose container system may involve a needle-based injection device with an integrated non-replaceable container. In such a system, each container holds multiple doses, the size of which may be fixed or variable (pre-set by the user).

As further described in ISO 11608-1: 2014 (E), a single-dose container system may involve a needle-based injection device with a replaceable container. In one example for such a system, each container holds a single dose, whereby the entire deliverable volume is expelled (full evacuation). In a further example, each container holds a single dose, whereby a portion of the deliverable volume is expelled (partial evacuation). As also described in ISO 11608-1: 2014 (E), a single-dose container system may involve a needle-based injection device with an integrated non-replaceable container. In one example for such a system, each container holds a single dose, whereby the entire deliverable volume is expelled (full evacuation). In a further example, each container holds a single dose, whereby a portion of the deliverable volume is expelled (partial evacuation).

The invention claimed is:

1. A medicament delivery device comprising:
a needle for injecting medicament;
a body having a proximal end and a distal end;
a needle cover, wherein the needle cover is proximally movable relative to the body from an initial position to a holding position in which the needle protrudes from the distal end of the needle cover for injecting medicament, and wherein the needle cover is distally movable relative to the body from the holding position to a locked position in which the needle cover covers the distal end of the needle;
a biasing member configured to bias the needle cover distally; and
a guide member configured to rotate relative to the needle cover,
wherein one of the guide member and the needle cover comprises a pin and the other of the guide member and the needle cover comprises a guide path for guiding the pin, wherein the guide path comprises a first ramp, a second ramp and a locking abutment surface,
wherein the pin is positioned at a first position when the needle cover is in the initial position, wherein the first position is external to the guide path, and wherein the first ramp is configured to engage the pin when the needle cover moves axially from the initial position towards the holding position for rotating the guide member relative to the needle cover,
wherein the pin is positioned at a second position when the needle cover is in the holding position, wherein the second ramp is configured to engage the pin when the needle cover moves axially from the holding position towards the locked position for rotating the guide member relative to the needle cover, and
wherein the pin is positioned at a third position when the needle cover is in the locked position, wherein the locking abutment surface is radially fixed relative to the guide member and configured to engage the pin to prevent the needle cover from moving proximally away from the locked position.

2. The medicament delivery device according to claim 1, wherein the locking abutment surface comprises a planar surface which is at an acute angle to the longitudinal axis of the medicament delivery device.

3. The medicament delivery device according to claim 1, wherein when the pin is in the second position it engages the first ramp.

4. The medicament delivery device according to claim 1, wherein the first position is in the guide path, and optionally wherein the guide path comprises an axially extending portion, wherein the first position is in the axially extending portion, and optionally wherein the axially extending portion is parallel with the longitudinal axis of the medicament delivery device.

5. The medicament delivery device according to claim 1, wherein the needle cover is rotationally fixed relative to the body and/or wherein the guide member is axially fixed relative to the body.

6. The medicament delivery device according to claim 1, wherein the first ramp comprises a planar surface which is at an acute angle to the longitudinal axis of the medicament delivery device and/or wherein the second ramp comprises a planar surface which is at an acute angle to the longitudinal axis of the medicament delivery device.

7. The medicament delivery device according to claim 1, wherein the body is configured to be gripped by a user.

8. The medicament delivery device according to claim 1, wherein the needle cover comprises the pin and the guide member comprises the guide path and/or wherein in the initial position the needle cover covers the distal end of the needle.

9. The medicament delivery device according to claim 8, wherein the guide member comprises an outer surface, and wherein the guide path is recessed within the outer surface.

10. The medicament delivery device according to claim 8, wherein the needle cover comprises an arm, wherein the pin is provided on the arm, and optionally wherein the pin is provided on the free end of the arm.

11. The medicament delivery device according to claim 1, wherein the first ramp is configured to rotate the guide member in a first direction when the needle cover moves axially away from the initial position towards the holding position, and wherein the second ramp is configured to rotate the guide member in the first direction when the needle cover moves axially from the holding position towards the locked position, and optionally wherein the locking abutment surface is configured to prevent rotation of the guide member in a second direction which is counter to the first direction when the pin is in the third position.

12. The medicament delivery device according to claim 1, wherein the medicament delivery device is configured to inject greater than 2 ml of medicament and/or wherein the medicament delivery device is configured to inject medicament having a viscosity of greater than 25 cP.

13. The medicament delivery device according to claim 1, wherein the device comprises a mechanism which automatically causes medicament to be dispensed from the device, wherein when the needle cover moves from the initial position towards the holding position it releases the mechanism and medicament is automatically dispensed from the device.

14. The medicament delivery device according to claim 1, wherein the device comprises the medicament.

15. A method of locking a medicament delivery device after medicament has been dispensed from the medicament delivery device, the method comprising moving a needle cover of the device to a locked position in which the needle cover covers the distal end of a needle of the device, wherein the device comprises a guide member configured to rotate relative to the needle cover, and wherein one of the guide member and the needle cover comprises a pin and the other of the guide member and the needle cover comprises a guide path for guiding the pin, wherein the pin is positioned at a first position when the needle cover is in an initial position, wherein the first position is external to the guide path, wherein the guide path comprises a locking abutment surface that is radially fixed relative to the guide member, and wherein when the needle cover is in the locked position then proximal movement of the needle cover away from the locked position is blocked by the pin engaging the locking abutment surface.

16. A method of using a medicament delivery device, the method comprising removing the medicament delivery device from an injection site, wherein removing the medicament delivery device from the injection site causes a needle cover of the device to move to a locked position in which the needle cover covers the distal end of a needle of the device, wherein the device comprises a guide member configured to rotate relative to the needle cover, and wherein one of the guide member and the needle cover comprises a pin and the other of the guide member and the needle cover comprises a guide path comprising a locking abutment surface that is radially fixed relative to the guide member, wherein the pin is positioned at a first position when the needle cover is in an initial position, wherein the first position is external to the guide path, and wherein when the needle cover is in the locked position then proximal movement of the needle cover away from the locked position is blocked by the pin engaging the locking abutment surface.

17. The method according to claim 16, further comprising the preceding step of pressing the medicament delivery device against the injection site to move the needle cover from the initial position to a holding position for dispensing medicament from the device.

18. The method according to claim 17, further comprising holding the medicament delivery device in the holding position whilst medicament is dispensed from the device.

19. The method according to claim 17, wherein the guide path further comprises a first ramp which engages the pin when the needle cover moves axially from the initial position towards the holding position for rotating the guide member relative to the needle cover.

20. The method according to claim 16, wherein the guide path further comprises a second ramp which engages the pin when the needle cover moves from the holding position towards the locked position for rotating the guide member relative to the needle cover.

* * * * *